United States Patent [19]

Sutterlin

[11] Patent Number: 5,667,506
[45] Date of Patent: Sep. 16, 1997

[54] SPINAL ROD TRANSVERSE CONNECTOR FOR SUPPORTING VERTEBRAL FIXATION ELEMENTS

[75] Inventor: Chester E. Sutterlin, Gainesville, Fla.

[73] Assignee: Danek Medical, Inc., Memphis, Tenn.

[21] Appl. No.: 404,118

[22] Filed: Mar. 14, 1995

Related U.S. Application Data

[63] Continuation of Ser. No. 966,100, Oct. 22, 1992, abandoned.

[51] Int. Cl.$^6$ ............................ A61B 17/56; A61B 17/58
[52] U.S. Cl. ............................ 606/61; 606/60; 606/72
[58] Field of Search .......................... 606/60, 61–65, 606/69, 70, 71, 72

[56] References Cited

U.S. PATENT DOCUMENTS

| | | | |
|---|---|---|---|
| 4,773,402 | 9/1988 | Asher | 606/61 |
| 4,887,595 | 12/1989 | Heinig et al. | |
| 5,002,542 | 3/1991 | Frigg | 606/61 |
| 5,092,893 | 3/1992 | Smith | 606/61 |
| 5,102,412 | 4/1992 | Rogozinski | |
| 5,108,395 | 4/1992 | Laurain | 606/61 |
| 5,127,912 | 7/1992 | Ray | 606/61 |
| 5,147,359 | 9/1992 | Cozad et al. | 606/60 |
| 5,209,752 | 5/1993 | Ashman et al. | 606/61 |
| 5,261,909 | 11/1993 | Sutterlin et al. | 606/60 |
| 5,403,316 | 4/1995 | Ashman | 606/61 |
| 5,480,442 | 1/1996 | Bertagnoli | 606/61 |
| 5,507,745 | 4/1996 | Logroscino et al. | 606/61 |

FOREIGN PATENT DOCUMENTS

| | | | |
|---|---|---|---|
| 1097303 | 6/1984 | U.S.S.R. | 606/65 |
| 9004948 | 5/1990 | WIPO | 606/61 |
| 94016635 | 8/1994 | WIPO | 606/61 |

OTHER PUBLICATIONS

"TSRH Lumbar System", Danek Medical, Inc., 1991.
"TSRH Crosslink Components", Danek Medical, Inc., 1990.

*Primary Examiner*—Robert A. Hafer
*Assistant Examiner*—Justine R. Yu
*Attorney, Agent, or Firm*—Woodard, Emhardt, Naughton Moriarty & McNett

[57] ABSTRACT

A spinal implant system includes a pair of spinal rods arranged on opposite sides of the spinous processes of a patient. An transverse connector assembly in accordance with the invention includes a plate having a central portion which spans between the spinal rods. At each end of the central portion is an integral body portion having an elongated slot formed therein. An eyebolt extending through the slot and has an opening to receive the spinal rod therethrough to clamp the spinal rod to a respective one of the body portions. At the end of each body portion distal from the central portion is an enlarged end piece having an end face oriented generally perpendicular to the longitudinal axis of the slot in the plate body. A threaded post extends from the end face and is used together with a nut to clamp the yoke portion of the vertebral fixation element to the plate. In another embodiment, an eyebolt assembly is used to mount a vertebral fixation element to an endpiece bar extending from the plate.

37 Claims, 3 Drawing Sheets

Fig. 1

(PRIOR ART)

SPINAL ROD TRANSVERSE CONNECTOR FOR SUPPORTING VERTEBRAL FIXATION ELEMENTS

This application is a continuation of application Ser. No. 07/966,100, filed Oct. 22, 1992, now abandoned.

BACKGROUND OF THE INVENTION

The present invention broadly concerns devices for use in spinal implant systems, particularly those using spinal rods contoured for connection at various locations along the length of the spinal column. More specifically, the invention concerns an apparatus for spanning between spinal rods to support vertebral fixation elements of the implant system which provide direct engagement to vertebrae of the spinal column.

Several techniques and systems have been developed for use in correcting and stabilizing spinal curves and facilitating spinal fusion. In one system, a bendable rod is longitudinally disposed adjacent the vertebral column and is fixed to various vertebrae along the length of the column by way of a number of fixation elements. A variety of fixation elements can be provided, such as hooks or bone screws, which are configured to engage specific portions of the vertebra. Typically, two such rod assemblies are used, one on each side of the spinous process or sagittal plane.

An example of one such system is the TSRH® spinal system of Danek Medical, Inc. In this system, hooks or screws are engaged to the spinal rod by way of eyebolts which are slidably disposed onto the spinal rod and captured within yokes on the fixation elements. A nut is threaded onto a threaded post of the eyebolt to clamp the yoke and rigidly fix the hook or screw element to the spinal fixation rod. Details of the TSRH spinal implant system are disclosed in the "Surgical Technique Manual" provided by Danek Medical, Inc., published in 1990, which disclosure is incorporated herein by reference.

Figure 1:
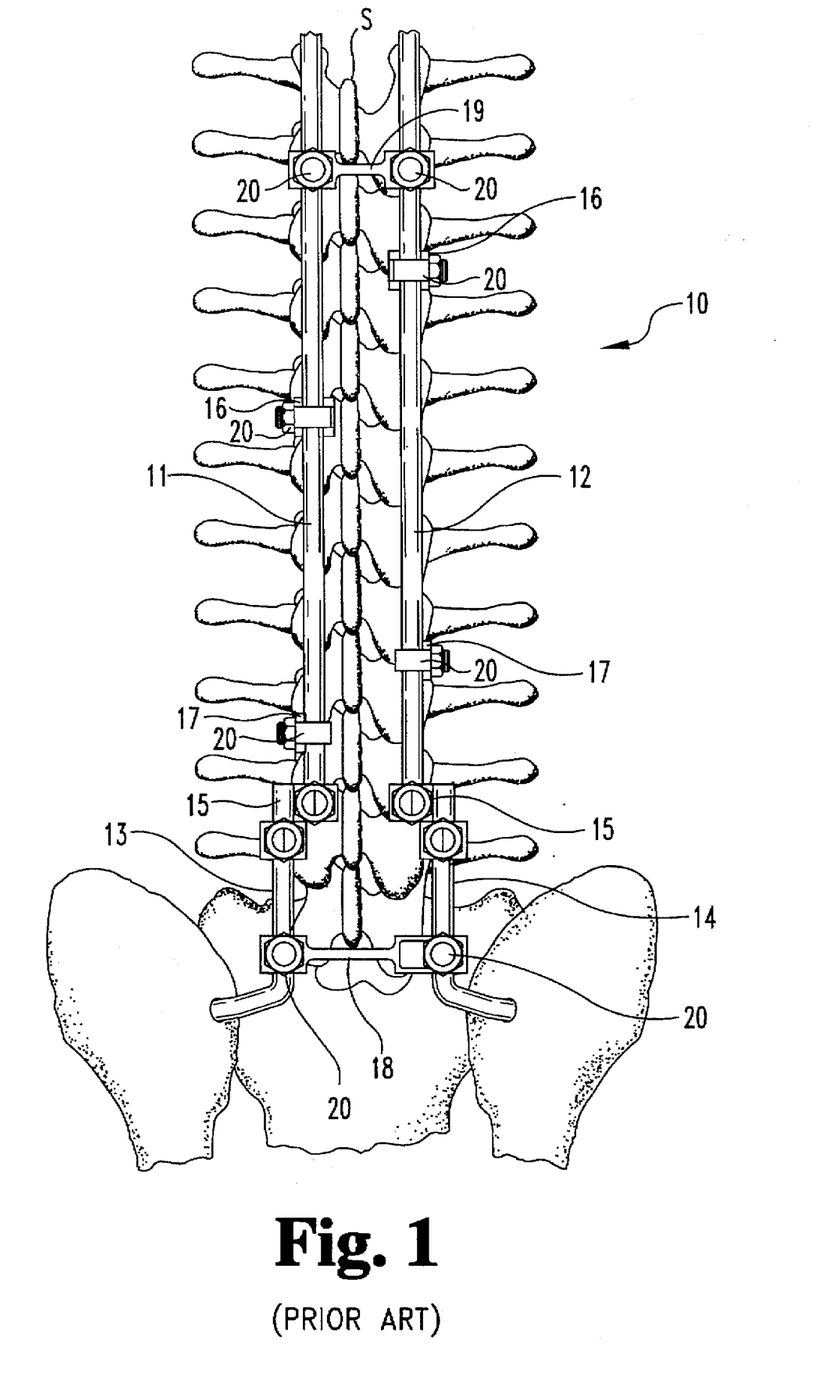
FIG. 1 is a top elevational view of a spinal rod fixation system such as the Danek TSRH® system of the prior art shown engaged about the spinal column of a patient.

One such construct of the TSRH® spinal system is shown in FIG. 1. In this construct 10, a pair of bendable spinal rods 11 and 12 extend along the vertebral column of a patient on either side of the sagittal plane or spinous process S. In the illustrated construct, the rods 11 and 12 are adjacent the lumbar vertebrae. These rods are connected to a second pair of rods 13 and 14 which engage the sacrum of the patient. The rods 11 and 13 on the left side of the spinous process S as well as the rods 12 and 14, can be engaged by a plate 15, which can be constructed as the CROSSLINK® lock plates 804-010 or 804-043 manufactured by Danek Medical, Inc. as part of its TSRH® system.

A number of vertebral fixation elements are fixed to the spinal rods along the length of the rods. For example, spinal hooks 16 can be disposed at certain positions along the right or left rods. These hooks can be similar to the Danek pedicle hooks 808-004 components of the TSRH® system. In addition, the vertebral fixation elements can be bone-engaging screws 17, such as the Danek anterior spinal screws sold as product number 808-225.

It has been discovered that in the post-operative period before fusion of the vertebrae occurs, a significant amount of motion can occur between the rods and the vertebral fixation elements, which motion can diminish the corrective effects of the spinal instrumentation 10. Thus, means are provided in the TSRH® system to laterally connect the rods across the sagittal plane to form a rigid "quadrilateral" construct. This means can include a plate 18, such as the CROSSLINK® plate produced by Danek Medical. This plate, as is described more fully in the above referenced "Surgical Technique Manual", rigidly interconnects the opposite rods to reduce the loss of correction that occurs over time. The plates 18 and 19 connected at distal locations along the rods are engaged to the rods by way of the same eyebolt assemblies 20 that are used to engage the vertebral fixation elements to the rod.

It is the goal of the surgeon using such spinal implant systems to apply the vertebral fixation elements (hooks and/or screws) to the spine in the appropriate anatomic position, and then to engage each fixation element to the spinal rod. Once the spinal implant system is assembled it is then possible to correct anatomical deformities and stabilize the spine. In the ideal circumstance, the fixation elements are located in a colinear position substantially parallel to the sagittal plane S. However, in many circumstances particular vertebrae may deviate from this colinear position. Under these circumstances, it is often necessary to contour the rod to account for abnormal lateral curvatures of the spine, such as scoliotic curvatures. After the rod has been contoured as dictated by the anatomy, the fixation hooks or bone screws can be engaged directly to the laterally offset vertebrae.

One difficulty with spinal fixation systems of the prior art, and particularly those utilizing spinal rods, is that lateral contouring of the rod in the sagittal plane can often be difficult, particularly since the rod must also be contoured to the normal cervical and lumbar curvatures of the spine. Three dimensional rod contouring is often physically difficult and is sometimes not possible in the space available for a particular patient.

The contouring required to accommodate the abnormal curvatures of the spine being treated often poses problems for engaging the vertebral fixation elements between the rod and the particular vertebra. This problem is particularly difficult with respect to bone screws. It has been found that fixation of the bone screws to the vertebra in a somewhat lateral approach is often preferable since it provides a more secure fixation at the pedicle of the vertebra and minimizes the risk to the spinal cord canal. However, typical spinal rod systems, such as the TSRH® system illustrated in FIG. 1, do not readily accommodate this partial lateral approach to engaging the bone screw between the vertebra and the spinal rod. Moreover, these systems are not easily adapted to the varying pedicle entry angles afforded at the different vertebral levels. Another drawback of systems such as the system 10 in FIG. 1 is that a number of different components are required to engage the vertebrae and to rigidly interconnect the opposite spiral rods across the sagittal plane.

It would therefore be desirable to have a more streamlined system with a minimum of separately implanted components to not only reduce the amount of time required to implant the system, but to also reduce the irritation to the surrounding soft tissue of the patient.

It is also desirable to have a spinal fixation system that is readily adapted to provide lateral coupling between spinal rods at multiple stages or segments of the spinal column. Such a system should provide this segmental interconnection without interfering with vertebral areas available for bone grafting to achieve permanent fixation or immobilization of damaged vertebrae.

There is currently no system known to the inventor that addresses each of these features in a single apparatus. There is further no known system that adequately provides for mounting a vertebral fixation element, such as a spinal screw, at a number of variable positions relative to the spinal rod, or that permits selective orientation of the fixation element through a number of degrees of freedom. The present invention addresses these needs as well as provides other benefits not previously found in spinal fixation systems of the prior art.

SUMMARY OF THE INVENTION

In accordance with the invention, an apparatus is provided for spanning between a pair of spinal rods implanted adjacent a patient's vertebrae along the sagittal plane. A number of vertebral fixation elements are engaged along the length of the rods to fix the rod to various vertebrae. In one aspect of the invention, the apparatus spanning between the rods includes means for engaging the rods and means, outboard of the rod engaging means, for engaging vertebral fixation elements at the ends of the apparatus. In a specific embodiment, the apparatus includes a plate having an elongated central portion spanning between the spinal rods. Integral with the ends of the central portion are the rod engaging portions which include a generally rectangularly shaped portion having an elongated slot therethrough to accept a rod engaging eyebolt. The bottom surface of the rectangular rod engaging portions can be scalloped to firmly locate the spinal rod relative to the plate.

At each end of the plate is a means for engaging the vertebral fixation element which includes an enlarged end piece. The face of the end piece includes a radially splined surface to mate with a similarly splined face on the head of the vertebral fixation element. A threaded post projects from the end piece to engage a machine nut to clamp the head of the vertebral fixation element to the end piece. The apparatus of the present invention thus incorporates features to connect vertebral fixation elements to the spinal rods, along with features to interengage or laterally connect the spinal rods to thereby form a generally rigid quadrilateral construct.

Another feature of the invention resides in the bend formed between the central spanning portion and the rod engaging portions of the plate. The angle of the bend allows the vertebral fixation elements to engage the vertebra at a transverse angle in accordance with conventional fixation techniques. This angle can be adjusted slightly by the surgeon during an implantation procedure by bending the plate to a precise angle dictated by the patient's anatomy. The splined end face of the fixation element engagement portions allow orientation of the vertebral fixation element at a sagittal angle as dictated by the patient's anatomy. The invention thus provides a "triangulated" or "delta" construct in which the fixation elements, typically bone screws, are interconnected and are oriented at lateral angles relative to the vertebra. This triangulated or delta construct results in an increase "grip" on the vertebral body, thereby permitting large manipulative forces to be exerted to correct anatomical deformities of the spine.

In another embodiment of the invention, a transverse connector apparatus includes a plate having a pair of rod-engaging portions separated by bending slots on opposite sides of the plate at the midline of the plate. The bending slots allow the plate to bent at the slot locations to an appropriate angle. Each of the rod-engaging portions include a slot having a countersunk portion. The slot is adapted to receive a bolt of a rod engagement means therethrough. The bolt includes a contoured head which fits within the countersunk portion of the slot. The bolt projects upwardly through the slot away from the vertebrae when the transverse connector assembly is implanted in position about the spine. A hook-shaped clamp extends over the bolt and includes a hook portion which is adapted to restrain a spinal rod between the clamp and the upper surface of the plate. A nut that engages the bolt to compress the clamp and rod assembly.

In one aspect of the transverse connector assembly of this embodiment, a pair of end pieces are connected to opposite ends of the plate, preferably integral with the plate. In the preferred embodiment, each of the end pieces is in the form of a bar oriented at an angle with respect to the plate. That angle can be similar to the angle achieved by the transverse connector assembly of the previous embodiment. Each of the bars provides a means for connection of the transverse connector assembly to a pair of vertebral fixation elements, such as bone screws. In particular, an eyebolt assembly can be provided to engage an open head, or yoke configured bone screw to the rod.

The transverse connector plate assembly of this further embodiment provides a high degree of variability in coupling vertebral fixation elements to spinal rods. For instance, the rod engagement means including the clamp interengaged with the slotted connector plate, allows lateral variation of the fixation of the spinal rod to the plate. The implementation of bar shaped endpieces, in combination with the eyebolt assembly attachment of the vertebral fixation element allows movement of the fixation element along the length of the rod, as well as rotation of the element about the axis of the rod. Another degree of variability is offered by the further variation of this embodiment of the invention which incorporates a variable angle screw configuration. In particular, the eyebolt assembly is used to mount a splined washer and a vertebral fixation element having a splined yoke to the end piece rod.

With this second embodiment of the invention, a wide range of fixation can be achieved coupled to a spinal rod. Selective positioning of the fixation element relative to the transverse connector plate can be achieved in several degrees of linear and rotational degrees of freedom. In addition, the transverse connector assembly of this embodiment provides similar benefits as the previous embodiment of the invention in that it allows for segmental interconnection of the spinal rods and engagement to different levels of vertebrae along the spinal column, without interfering with the area between the transverse processes that can be made available for bone grafting.

It is one object of the invention to provide an apparatus for use in laterally connecting spinal rods implanted adjacent a patient's vertebral column. A further object is to combine this feature with features to engage vertebral fixation elements.

Another object of the invention resides in providing support for the vertebral fixation elements that allows a lateral angle entry into a vertebra. Yet another object concerns allowing angulation of the vertebral fixation element in the sagittal and lateral senses or variable positioning of the fixation element with respect to the rods in several degrees of freedom to accommodate the patient's vertebral anatomy.

One benefit of the apparatus of the present invention is that it combines means for connecting the vertebral fixation elements to the spinal rods with means for laterally or transversely connecting the spinal rods together. An additional benefit is that a more compact construct is provided versus prior spinal rod constructs employing many individual components to connect vertebrae and spinal rods.

Yet another benefit achieved by the invention resides in providing segmental coupling or connection of the spinal rods, while permitting a wide variation of orientations of the vertebral fixation elements relative to the spinal rods.

Other objects and further benefits of the present invention will become apparent to persons of ordinary skill in the art from the following written description and accompanying figures.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
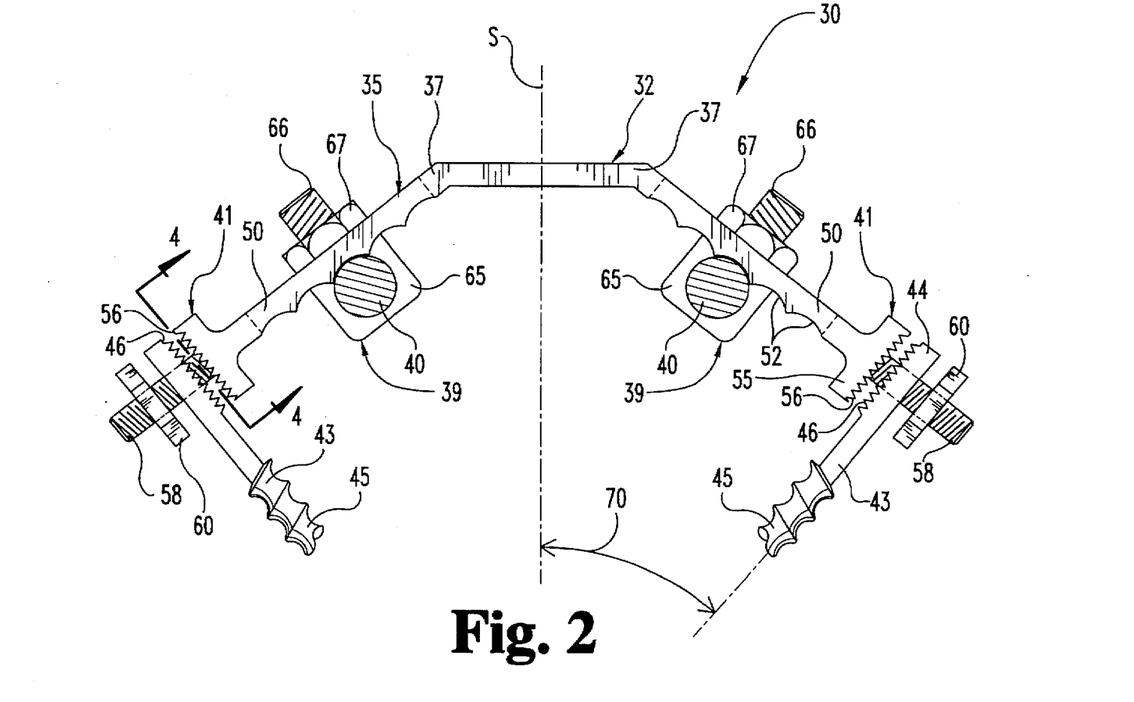
FIG. 2 is a side elevational view of the transverse connector apparatus of the present invention spanning between two spinal rods with a pair of vertebral fixation screws engaged between the apparatus and a vertebra of the patient.
Figure 3:
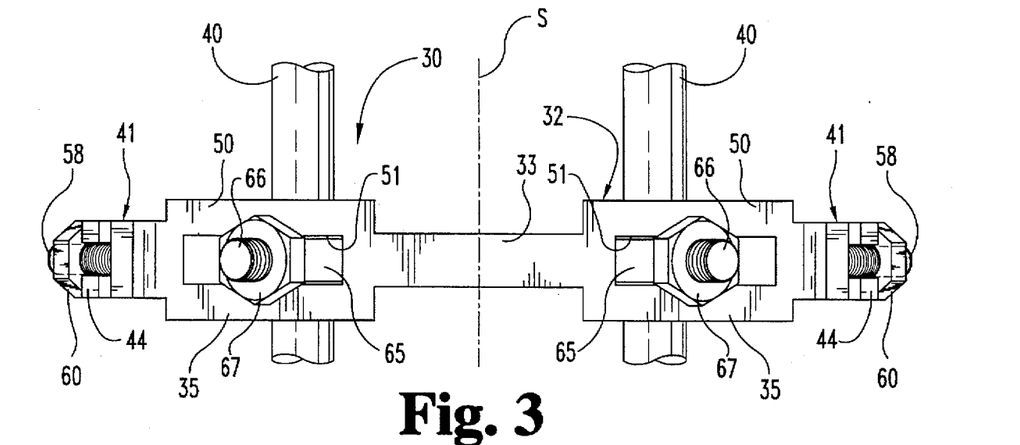
FIG. 3 is a top elevational view of the apparatus as shown in FIG. 2 connected between the spinal rods.
Figure 4:
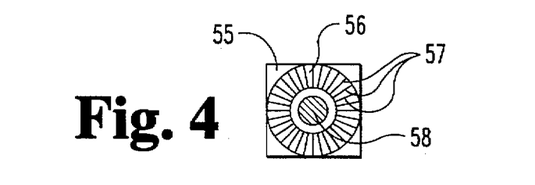
FIG. 4 is an end partial cross-sectional view of one end of the transverse connector apparatus shown in FIGS. 2 and 3.

A transverse connector assembly 30 in accordance with one embodiment of the present invention is depicted in FIGS. 2–4. The assembly 30 includes an elongated plate 32 which is configured to span between the spinal rods 40 across the spinous process at sagittal plane S. The plate 32 includes a central spanning portion 33 which is integral at its ends with a pair of rod-engaging portions 35. The length of the central spanning portion can be determined by the transverse distance between the spinal rods straddling the spinous processes S as dictated by the anatomy. The central portion 33 preferably has a width that is less than the width of the rod-engaging portions 35 so that the plate 32 has a reduced profile immediately adjacent the spinous process. The rod-engaging portions 35 are connected to the central spanning portion 33 at a pair of plate bends 37. The plate bends 37 orient the vertebral fixation elements at an optimum angle for engaging the pedicle of the vertebrae, as discussed in more detail herein.

The plate 32 further includes a fixation element connection means or screw engagement portion 41 at each end of the rod engagement portions 35, distal from the central spanning portion 33. In other words, the screw engagement portions are situated at the outside ends of the plate 32. Each screw engagement portion 41 is configured to engage a vertebral fixation element 43, which in the illustrated preferred embodiment is a spinal screw. It is understood, however, that other vertebral fixation elements may be utilized. In the present embodiment, the vertebral fixation element, or spinal screw 43, includes an open-top yoke 44 and a bone-engaging portion 45. In this respect the screw 43 is configured similar to the TSRH® open head bone screw 808-225 through 475 provided by Danek Medical, Inc. The yoke 44 allows the plate 32 to be "top loaded"—that is, the transverse connector assembly 30 can be implanted over the screw after the screw has been engaged in the vertebra. A similar yoke can be implemented on other vertebral fixation elements, such as a spinal hook. The screw 43 is modified from the standard TSRH® bone screw to include a radially splined face 46 for reasons explained more fully herein.

Referring to the rod-engaging portions 35 of the plate 32 in more detail, the portions include a body 50 which is generally rectangular in shape and which has a width greater than the width of the central spanning portion 33. A slot 51 is defined in each of the bodies 50 which extends generally longitudinally along the lengthwise axis of the plate 32. The underside of the body 50 is formed to define a number of scallops 52 which are configured to engage the spinal rods 40 in a manner well known in the art. For example, each scallop 52 is generally formed at a radius that is slightly smaller than the radius of the spinal rod 40 which is to be situated within the scallop. In the illustrated embodiment, the plate body 50 includes five such scallops evenly spaced along the length of the slot 51 to accommodate a number of different positions of the spinal rods 40 relative to the transverse connector assembly 30 and particularly the plate 32. The scallops provides means for fixing the spinal rods so that the rods and plate do not shift relative to each other along the longitudinal axis of the plate 32. However, it is understood that the underside of the plate body 50 may be smooth and that other means may be provided to firmly fix the spinal rods 40 relative to the plate body 50 and slot 51.

Details of the fixation element connection means or screw engagement portions 41 are shown most particularly in FIGS. 2 and 4. The screw-engagement portions 41, as previously described, are each disposed at the ends of the rod engagement means 39 at either side of the plate 32. The portions 41 include an end piece 55 which is flared outwardly from the plate body 50 into a generally rectangular shape. The end face 56 of each end piece 55 includes a number of radial splines 57. These radial splines are configured to engage the splined face 46 of the vertebral fixation element 43.

As shown more clearly in FIG. 4, the radial splines 57 are generally oriented in an annular ring around the end face 56 of the end piece 55. The end piece 55 further includes a mounting post 58 which extends outwardly from the center of the end face 56 and which includes machine threads to engage a threaded nut 60. As shown in FIG. 2, the mounting post 58 and threaded nut 60 are used to clamp the vertebral fixation element 43, and particularly the yoke, between the nut 60 and end piece 55. It is understood that the interaction of the radially splined faces 46 and 57 allow the angular orientation of the vertebral fixation element to be varied prior to clamping by the nut 60. This variable angle feature provides greater flexibility in engaging the vertebral fixation element 43 to portions of a vertebrae, such as the pedicle, particularly where the rod is bent to complicated three-dimensional curvatures. With this variable angle feature, the plate 32 can be optimally oriented to avoid anatomical features of the vertebral column while still providing adequate access to the vertebra for fixation.

The transverse connector assembly 30 includes rod-engagement means 39 which are used to fix the plate 32 to the spinal rods 40. In the preferred embodiment, each rod-engagement means 39 includes a eyebolt 65 which is configured to extend into the slot 51 of the plate body 50. A threaded stem 66 projects from the eyebolt 65 and through the slot 51 for engagement by a threaded nut 67. The eyebolt 65 and nut 67 of the preferred embodiment can be substantially similar to the TSRH® eyebolt assembly product number 808-027 through 030 provided by Danek Medical for use with its TSRH® fixation system. However, it is understood that any similar means can be provided for engaging the rod 40 to the plate body 50, particularly within the scallops 52. In the preferred embodiment, tightening down the nut 60 along the mounting post 58 draws the eyebolt toward the plate body, and thereby clamps the spinal rod 40 between the base of the eyebolt opening and the scallops 52 of the plate body 50.

The transverse connector assembly 30 of the present invention provides significant advantages when used in connection with spinal rod implant systems. In particular, the assembly 30 combines the rigid lateral connection between spinal rods with means for engaging a vertebral fixation element that is mounted in a vertebra of the spine. The assembly 30 further provides ready means for creating a rigid rectangular construct that is generally not susceptible to loosening over time.

One significant benefit is provided by the configuration of plate 32 in which the central spanning portion 33 has a minimal profile while the remainder of the assembly is oriented at an angle relative to the spinous process or sagittal plane S to provide a somewhat lateral fixation of the vertebral fixation elements. The angle of the rod-engaging portions 39, and particularly plate bodies 50, as they extend from the plate bend 37, can be predetermined when the plate is made to accommodate a number of different fixation element alignments. It has been found that a preferred lateral fixation angle 70 (FIG. 2) relative to the sagittal plane S falls between 5 degrees and 25 degrees for each of the successive lumbar vertebrae, for instance. Thus, a number of plates 32 can be provided in which the fixation angle 70 as embodied within the plate bend 37, is varied.

The plate 32 is preferably formed of medical grade stainless steel or similar high-strength material. It is also preferred that the plate material have some flexibility, since it has been found that some flexibility in spiral fixation components provides beneficial healing results. Moreover, a certain amount of bendability of the plate 32 allows for minor adjustments in the configuration of the plate 32 and particularly the fixation angle 70 for the vertebral fixation elements 43 as may be required by the spinal anatomy. In some instances, it has been found that that the plate also must be twisted somewhat about its longitudinal axis in order to accommodate the spinal features. However, the use of the splined face 46 on the fixation element 43 mating with the radial splines 57 of the screw-engagement portion 41 provides a variable angle feature to the fixation that may eliminate the need for twisting the plate itself.

In one modification, the bend 37 between the central spanning portion 33 and the rod engaging portion 35 may instead be situated between the rod engaging portion and the enlarged end piece 41 to provide the lateral angle for the vertebral fixation element. Alternatively, two bends can be provided at either end of the rod engaging portion 35.

Figure 5:
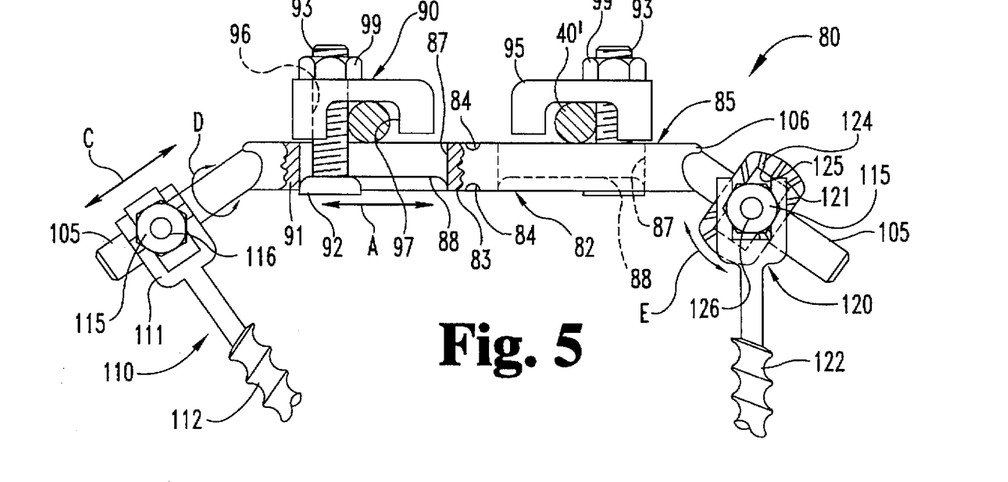
FIG. 5 is a side elevational view of a further embodiment of the transverse connector apparatus of the present invention spanning between two spinal rods with a pair of vertebral fixation screws engaged between the apparatus and a vertebra of the patient.

An additional embodiment of the invention is described with reference to FIGS. 5 and 6. In particular, a transverse connector assembly 80 includes a substantially flat plate 82 which is adapted to span between a pair of spinal rods 40' (which rods can be identical to the rods 40 in the previous figures). The plate 82 includes a central portion 83 between a pair of rod engaging portions 85. A bending notch 84 is formed on either of the opposite faces of the plate at the central portion 83. The bending notches provide a region of reduced thickness which facilitates bending of the plate 82 at the center of the plate. Thus, the plate 82, although initially planar, can be bent so that the rod engaging portions 85 are oriented at a lateral angle in a fashion similar to that shown in FIG. 2 regarding the prior embodiment.

Each of the rod engaging portions includes a slot 87 defined through the plate. The slot includes a countersink portion 88 at the lower surface of the plate. The slot 87 is configured to be used in conjunction with rod engagement means 90 to fix the fixation rod 40' to the plate 82. In particular, the rod engagement means 90 includes a fastener, such as a bolt 91 having a contoured head 92. The bolt is extend through the slot 87 with the contoured head 92 resting against the countersunk portion 88 of the slot. The rod engagement means 90 further includes a clamp 95 which in the preferred embodiment is in the shape of a "C". The clamp includes a bolt bore 96 through which the bolt 91 extends. A nut 99 can then be threaded onto the threaded shank 93 of the bolt to compress the clamp 95 and the rod 40'. The clamp 95 includes a hook portion 97 which is sized to surround and restrain the rod 40' from lateral movement relative to the plate 82.

The slot 87 and rod engagement means 90 provides for a great degree of variation in the coupling of the plate 82 to the spinal rods 40'. For instance, the slot 87 allows the bolt 91 to be moved back and forth within the slot to be fixed at any location in the slot. This linear degree of freedom movement of the bolt 91 is designated by the double arrows A. In addition, the clamp 95 can be rotated to any position relative to the plate by simply pivoting the bolt bore 96 about the bolt 91. For example, the clamp can be rotated 180° to face either left or right, as evidenced by the two clamps 95 shown in FIG. 5. In addition, the clamp can be rotated at angles less than 180° along an arc, designated as "B" in FIG. 6. Under some circumstances, the spinal rod 40' may have some curvature perpendicular to the sagittal plane "S", which curvature can be readily accommodated by orienting the clamp at a necessary angle to fix the rod to the plate.

In this second embodiment, the fixation element connection means is accomplished by way of an endpiece 105 affixed at the opposite ends of the plate 82. In this preferred embodiment, the endpiece 105 is in the form of a bar, preferably cylindrical in shape. The endpiece bar 105 can be attached to the plate 82 at a joint 106 which can be oriented at a bend angle, similar to the bend angle 37 of the embodiment shown in FIG. 2. Thus, this bend joint 106 orients the endpiece bar 105 at an angle to permit partial lateral engagement of the vertebral fixation element 110 with a corresponding vertebra, without the need necessarily to bend the plate 82 at the bending notches 84. However, steeper lateral angles entry of the vertebral fixation element can be achieved by bending the plate 82 in combination with the bend at the joint 106 between the endpiece rod 105 and the plate 82.

As in the previous embodiment, a vertebral fixation element 110 can be engaged to the transverse connector assembly 80. In particular, this fixation element 110 can be a bone screw having a yoke 111 or open head and a bone threaded portion 112. In this embodiment, the vertebral fixation element 110 is engaged to the endpiece bar 105 by way of an eyebolt assembly 115. The eyebolt assembly 115 call be substantially similar to the eyebolt assembly 65 previously described.

In one important aspect of this embodiment, the combination of the endpiece bar 105 and the eyebolt assembly 115 provides means for connecting the vertebral fixation element 110 to the transverse connector assembly 80 that allows for two degrees of freedom to orient the fixation element 110. In one degree of freedom, the eyebolt assembly 115 along with the fixation element 110 can be moved longitudinally in the direction C along the length of the endpiece bar 15. In addition, the fixation element and eyebolt assembly can be rotated in the direction D about the axis of the rod 105. In this manner, the transverse connector assembly 80 of this second embodiment allows for multiple linear and rotational degrees of freedom of movement to achieve a wide range of configurations and angles of the vertebral fixation element 110 with respect to the the tranverse plate 82. In this manner, the present embodiment is readily adapted to a wide range of anatomies and spinal conditions. Alternatively, the endpiece bars 105 can have a non-circular shape which can co-act with a correspondingly shaped opening in the eyebolt 115 to prevent rotation of the eyebolt and therefore the fixation element 110 relative to the bar.

In one version of the present embodiment, vertebral fixation elements 110 can be engaged at the endpiece bars 105 at each end of the transverse connector portion 82. An additional degree of freedom can be provided by substituting a variable angle screw assembly 120 for the vertebral fixation element 110. In this version, a variable angle screw includes a splined yoke 121 and a bone threaded portion 122. The splined washer 124 is also provided having an eyebolt opening 125. An eyebolt assembly 115 can be engaged on the rod endpiece 105 with a portion of the eyebolt extending through the eyebolt opening 125 of the splined washer 124. The splined yoke 121 of the variable angle screw can then be blocked against the endpiece bar 105 by way of a nut 126. Thus, as can be seen in FIG. 5, the variable angle screw assembly 120 adds a pivoting degree of freedom E that is not available with the vertebral fixation element 110. One design of a variable angle screw assembly 120 which can be implemented in this embodiment of the invention, is shown and described in copending application Ser. No. 07/836,362, on which the present inventor is a co-inventor. This application, which was filed on Feb. 18, 1992, provides more details of the construction of this variable angle screw assembly, which description is incorporated herein by reference.

Figure 6:
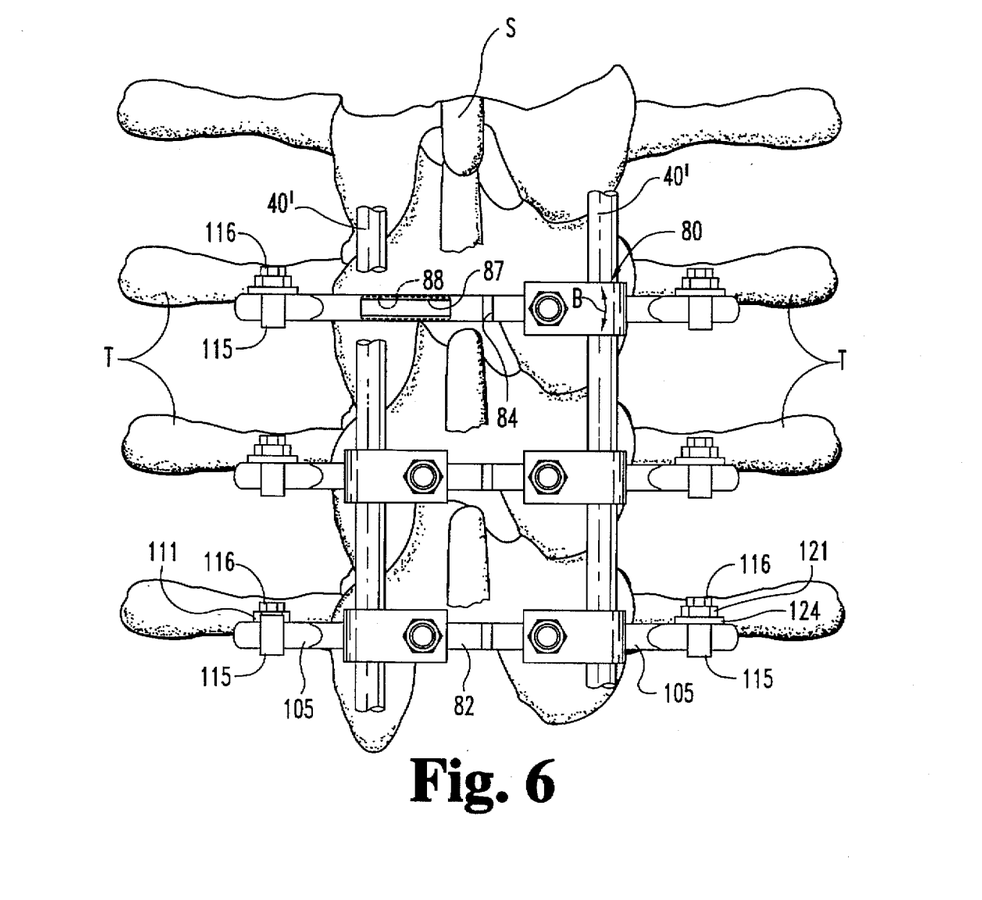
FIG. 6 is a top elevational view of the apparatus shown in FIG. 5 connected between spinal rods and engaged to the vertebrae of the patient.

Referring now to FIG. 6, the implementation of the transverse connection assembly of connector assembly 80 of this embodiment is depicted. In particular, it can be seen that a transverse connector assembly 80 is engaged at each level or segment of the vertebral column. The lowermost connector assembly includes a combination of the variable angle assembly 120 at one end of the plate 82 with a standard open yoke screw 111 on the left side of the plate. In each case, it can be seen that an eyebolt assembly 115 and nut 116 are used to engage either the vertebral fixation element 110 or the variable angle screw assembly 20 to a corresponding endpiece rod 105. It can be further seen from this figure that this segmental fixation requires some modification of the spinous process to provide clearance for passage of the plate 82 between the two rods 40'. However, it can be envisioned that clearance for the spinous process S can be achieved by bending the plate 82 at the bending slots 84 to clear this portion of the vertebrae. Adding additional angular orientation to the endpiece bars 105 in this manner may require the use of variable angle screw assemblies 120 at both endpiece bars 105 so that the angle of the vertebral fixation element relative to the transverse connector assembly 80 can be reduced for a proper entry angle into the vertebrae. As can be seen from FIG. 6, the transverse connector assembly 80 of this embodiment provides for a strong quadrilateral construct in a segmental lateral fixation, while still leaving adequate space between the transverse processes T of adjacent vertebrae for bone grafting as required.

It is understood that each of the components of the transverse connector assemblies 30 and 80 of the present invention are formed of a medical grade of material. Preferably, the components are formed of a medical grade stainless steel. Other materials are contemplated provided the material is strong enough to endure the high loads transmitted through the components, and yet is biocompatible.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A transverse connector assembly for spanning between a plurality of spinal rods situated adjacent a patient's vertebrae, said assembly comprising:

at least one vertebral fixation element having a bone engagement portion;

a plate including;

an elongated central portion having two opposite ends;

a pair of rod engaging portions, one each integrally disposed at each of said opposite ends of said central portion, each of said rod engaging portions having a longitudinal axis substantially transverse to the rods when said portions are engaged to the rods and a plurality of lateral locations adapted to receive a spinal rod, said locations spaced along the longitudinal axis of each of said rod engaging portions; and a pair of fixation element engagement portions configured for engaging said vertebral fixation element, one each of said fixation element engagement portions being affixed to a corresponding one of said pair of said rod engaging portions distal from said central portion; and rod engaging means for variably engaging said plate to at least one of the plurality of spinal rods at one of plurality of locations along a corresponding one of said rod engaging portions between said central portion and a corresponding one of said pair of fixation element engagement portions.

2. The transverse connector assembly of claim 1, wherein:

each of said pair of rod engaging portions includes an elongated body portion defining an elongated slot therethrough; and said rod engaging means includes means extending through said slot for clamping said at least one of the plurality of rods against a surface of said body portion.

3. The transverse connector assembly of claim 2, wherein said means for clamping includes:

an eyebolt defining an opening for receiving the spinal rod therethrough, said eyebolt having a threaded post for projecting through said elongated slot in said body portion; and a nut for threadedly engaging said eyebolt post to engage said eyebolt to said plate with the spinal rod extending through said opening.

4. The transverse connector assembly of claim 2, wherein said surface includes a number of scallops defined thereon and configured to receive a spinal rod therein, each of said number of scallops defining a cylindrical axis perpendicular to the longitudinal axis of said elongated slot.

5. The transverse connector assembly of claim 2, wherein said central portion has a width less than the width of said body portion of each of said pair of rod engaging portions.

6. The transverse connector assembly of claim 2, wherein said means for clamping includes:
   a fastener having a stem sized to extend through said elongated slot and a head portion sized to be retained against said body portion;
   a clamp defining a bore for receiving said stem of said fastener therethrough and having a hook portion configured to engage a spinal rod; and
   means for engaging said stem to connect said clamp to said fastener and to compress said rod between said hook portion and said body portion.

7. The transverse connector assembly of claim 6, wherein:
   said elongated body portion defines a countersunk portion around a perimeter of said elongated slot; and
   said head portion of said fastener is sized to be received within said countersunk portion without extending through said slot.

8. The transverse connector assembly of claim 1, wherein said plate includes a bend between said central portion and each of said pair of fixation element engagement portions to orient said vertebral fixation element at a lateral angle for engagement with a vertebra when said fixation element is engaged to said plate.

9. The transverse connector assembly of claim 8, wherein said bend is at each of said opposite ends of said central portion.

10. The transverse connector assembly of claim 8, wherein each said bend is between one of said rod engaging portions and a corresponding one of said fixation element engagement portions.

11. The transverse connector assembly of claim 1, wherein said central portion includes a reduced width portion that can be more readily bent in the plane of said plate than the remainder of said plate.

12. The transverse connector assembly of claim 1, wherein:
   each of said pair of fixation element engagement portions includes;
      an end piece having an end face;
      a threaded mounting post projecting from said end face; and
      a nut for threadedly engaging said threaded mounting post; and
   said at least one vertebral fixation element further includes
      a head portion attached to said bone engagement portion of said vertebral fixation element, said head portion having an opening to receive said threaded mounting post therethrough,
   wherein said head portion of said fixation element is clamped between said end face and said nut when said head portion is received over said mounting post and said nut is tightened onto said mounting post.

13. The transverse connector assembly of claim 12, wherein:
   said end face is oriented perpendicular to the longitudinal axis of said elongated body portion; and
   said threaded mounting post of each of said pair of fixation element engagement portions extends parallel to the longitudinal axis of said elongated body portion.

14. The transverse connector assembly of claim 12, wherein:
   said end face of said end piece includes several radial splines; and
   said head portion of said vertebral fixation element includes several corresponding radial splines for interdigitated engagement with the radial splines on said end face.

15. The transverse connector assembly of claim 1, wherein:
   each of said pair of fixation element engagement portions affixed to said rod engaging portion is configured as an elongated bar; and
   each of said pair of fixation element engagement portions includes means for variably engaging said vertebral fixation element along the longitudinal length of said elongated bar.

16. The transverse connector assembly of claim 15, wherein:
   said means for variably engaging includes;
      an eyebolt having an opening for receiving said elongated bar therethrough and a threaded mounting post projecting therefrom; and
      a nut for threadedly engaging said threaded mounting post; and
   said at least one vertebral fixation element includes;
      a bone engaging portion; and
      a head portion, said head portion having an opening to receive said threaded mounting post therethrough,
   wherein said head portion of said fixation element is clamped between said elongated bar and said nut when said head portion is received over said mounting post and said nut is tightened onto said mounting post.

17. The transverse connector assembly of claim 16, wherein:
   each of said pair of fixation element engagement portions includes a washer having an opening for receiving said eyebolt therethrough and a face having several radial splines; and
   said head portion of said fixation element includes several correspond radial splines for interdigitated engagement with the radial splines of said washer when said head portion is clamped with said washer between said nut and said elongated bar.

18. A transverse connector assembly for attaching a vertebral fixation element to a pair of spinal rods situated on opposite sides of spinous processes of a patient, said assembly comprising:
   a plate including;
      an elongated central portion having opposite ends;
      a pair of rod engaging portions, one each integrally disposed at each of said opposite ends of said central portion, each of said rod engaging portions having a longitudinal axis and a plurality of locations adapted to receive a spinal rod, said locations spaced along the longitudinal axis of each of said rod engaging portions; and
      a pair of fixation element engagement portions configured for connecting the vertebral fixation element to said plate, each of said fixation element engagement portions being integral with one of said rod engaging portions distal from said central portion; and
   rod engaging means for variably engaging said plate to each of the pair of rods at a plurality of locations along a corresponding one of said rod engaging portions between said central portion and said fixation element engagement portion to support each of the rods at variable distances from each other on opposite sides of the spinous process of the patient, wherein said central portion of said plate has a length sufficient to span across the spinous process when said plate is engaged to the pair of rods.

19. The transverse connector assembly of claim 18, wherein:
each of said pair of rod engaging portions includes an elongated body portion defining an elongated slot therethrough; and
said rod engaging means includes means extending through said slot for clamping one of the rods against a surface of said body portion.

20. The transverse connector assembly of claim 19, wherein said means for clamping includes:
an eyebolt defining an opening for receiving a spinal rod therethrough, said eyebolt having a threaded post for projecting through said elongated slot in said body portion; and
a nut for threadedly engaging said eyebolt post to engage said eyebolt to said plate with the spinal rod extending through said opening.

21. The transverse connector assembly of claim 19, wherein said surface of said plate body portion includes a number of scallops defined thereon and configured to receive a spinal rod therein, each of said number of scallops defining a cylindrical axis perpendicular to the longitudinal axis of said elongated slot.

22. The transverse connector assembly of claim 19, wherein said central portion has a width less than the width of said body portion of each of said pair of rod engaging portions.

23. The transverse connector assembly of claim 18, wherein said plate includes a bend between said central portion and each of said pair of fixation element engagement portions to orient said vertebral fixation element at a lateral angle for engagement with a vertebra when said fixation element is engaged to said plate.

24. The transverse connector assembly of claim 23, wherein said bend is at each of said opposite ends of said central portion.

25. The transverse connector assembly of claim 18, wherein:
each of said pair of fixation element engagement portions includes;
an end piece having an end face;
a threaded mounting post projecting from said end face; and
a nut for threadedly engaging said threaded mounting post; and
said at least one vertebral fixation element further includes
a head portion attached to said bone engagement portion of said vertebral fixation element, said head portion having an opening to receive said threaded mounting post therethrough,
wherein said head portion of said fixation element is clamped between said end face and said nut when said head portion is received over said mounting post and said nut is tightened onto said mounting post.

26. The transverse connector assembly of claim 25, wherein:
said end face is oriented perpendicular to the longitudinal axis of said elongated body portion; and
said threaded mounting post of said fixation element engagement portions extends parallel to the longitudinal axis of said elongated body portion.

27. The transverse connector assembly of claim 25 in which the vertebral fixation element has a head portion with several radial splines, wherein said end face of said end piece includes several corresponding radial splines for interdigitated engagement with the radial splines on the head portion of the fixation element.

28. A system including a plurality of vertebral fixation elements for attachment to a spine to correct and support the spine in treatment of spinal abnormalities, said system comprising:
a pair of spinal rods;
an elongated plate having a longitudinal length sufficient to span the spinous processes of a patient, and including;
an elongated central portion having opposite ends;
a pair of rod engaging portions, one each integrally disposed at each of said opposite ends of said central portion, each of said rod engaging portions having a longitudinal axis and a plurality of locations adapted to receive a spinal rod, said locations spaced along the longitudinal axis of each of said rod engaging portions; and
a fixation element engagement portion for engaging one of the plurality of vertebral fixation elements, having a portion connected with one of said rod engaging portions distal from said central portion; and means for variably engaging said plate to each of the pair
of rods at a plurality of locations along a corresponding one of said rod engaging portions to support said pair of rods at variable distances from each other on opposite sides of the spinous process of the patient.

29. The system of claim 28, wherein said fixation element engagement portion is oriented at an angle relative to the longitudinal axis of said elongated central portion.

30. The system of claim 28 wherein said fixation element engagement portion includes means for varying the angular orientation of a vertebral fixation element enagaged to said fixation element engagement portion relative to said plate in a plane perpendicular to the longitudinal axis of said plate.

31. The system of claim 28 wherein said fixation element engagement portion includes means for varying the orientation of a vertebral fixation element engaged to said fixation element engagement portion relative to said plate in one linear degree of freedom and one rotational degree of freedom.

32. The system of claim 28 wherein said fixation element engagement portion includes means for varying the orientation of a vertebral fixation element engaged to said fixation element engagement portion relative to said plate in one linear degree of freedom and two mutually perpendicular rotational degrees of freedom.

33. A transverse connector assembly for spanning between a plurality of spinal rods situated adjacent a patient's vertebrae, said assembly comprising:
at least one vertebral fixation element having a bone engagement portion;
a plate including;
an elongated central portion having two opposite ends;
a pair of rod engaging portions, one each integrally disposed at each of said opposite ends of said central portion, each of said rod engaging portions having a longitudinal axis and a plurality of locations adapted to receive a spinal rod, said locations spaced along the longitudinal axis of each of said rod engaging portions, each of said pair of rod engaging portions including an elongated body portion defining an elongated slot therethrough, said central portion having a width less than the width of said body portion of each of said pair of rod engaging portions; and a pair of fixation element engagement portions configured for engaging said vertebral fixation element, one each of said fixation element engagement portions being affixed to a corresponding one of said pair of said rod engaging portions distal from said central portion; and rod engaging means for variably engaging said plate to at least one of the plurality of spinal rods at one of said plurality of locations along a corresponding one of said rod engaging portions between said central portion and a corresponding one of said pair of fixation element engagement portions, said rod engaging means including means extending through said slot for clamping said at least one of the plurality of rods against a surface of said body portion.

34. A transverse connector assembly for spanning between a plurality of spinal rods situated adjacent a patient's vertebrae, said assembly comprising:

at least one vertebral fixation element having a bone engagement portion;

a plate including;

an elongated central portion having two opposite ends;

a pair of rod engaging portions, one each integrally disposed at each of said opposite ends of said central portion, each of said rod engaging portions having a longitudinal axis and a plurality of locations adapted to receive a spinal rods said locations spaced along the longitudinal axis of each of said rod engaging portions, each of said pair of rod engaging portions including an elongated body portion defining an elongated slot therethrough, said elongated body portion defining a countersunk portion around a perimeter of said elongated slot; and a pair of fixation element engagement portions configured for engaging said vertebral fixation element, one each of said fixation element engagement portions being affixed to a corresponding one of said pair of said rod engaging portions distal from said central portion; and rod engaging means for variably engaging said plate to at least one of the plurality of spinal rods at one of said plurality of locations along a corresponding one of said rod engaging portions between said central portion and a corresponding one of said pair of fixation element engagement portions, said rod engaging means including clamping means extending through said slot for clamping said at least one of the plurality of rods against a surface of said body portion, said clamping means including a fastener having a stem sized to extend through said elongated slot and a head portion sized to be retained against said body portion, said head portion sized to be received within said countersunk portion without extending through said slot a clamp defining a bore for receiving said stem of said fastener therethrough and having a hook portion configured to engage one of the spinal rods, and means for engaging said stem to connect said clamp to said fastener and to compress one of the spinal rods between said hook portion and said body portion.

35. A transverse connector assembly for spanning between a plurality of spinal rods situated adjacent a patient's vertebrae, said assembly comprising:

at least one vertebral fixation element having a bone engagement portion;

a plate including;

an elongated central portion having two opposite ends, said central portion includes a reduced width portion that can be more readily bent in a plane of said plate than the remainder of said plate;

a pair of rod engaging portions, one each integrally disposed at each of said opposite ends of said central portion, each of said rod engaging portions having a longitudinal axis and a plurality of locations adapted to receive a spinal rod, said locations spaced along the longitudinal axis of each of said rod engaging portions; and a pair of fixation element engagement portions configured for engaging said vertebral fixation element, one each of said fixation element engagement portions being affixed to a corresponding one of said pair of said rod engaging portions distal from said central portion; and rod engaging means for variably engaging said plate to at least one of the plurality of spinal rods at one of said plurality of locations along a corresponding one of said rod engaging portions between said central portion and a corresponding one of said pair of fixation element engagement portions to support the rods at variable distance from each other on opposite sides of a spinous process of the patient.

36. A transverse connector assembly for attaching a vertebral fixation element to a pair of spinal rods situated on opposite sides of spinous processes of a patient, said assembly comprising:

a plate including;

an elongated central portion having opposite ends;

a pair of rod engaging portions, one each integrally disposed at each of said opposite ends of said central portion, each of said rod engaging portions having a longitudinal axis and a plurality of locations adapted to receive a spinal rod, said locations spaced along the longitudinal axis of each of said rod engaging portions, each of said pair of rod engaging portions including an elongated body portion defining an elongated slot therethrough;

said central portion having a width less than a width of said body portion of each of said pair of rod engaging portions; and a pair of fixation element engagement portions configured for connecting the vertebral fixation element to said plate, each of said fixation element engagement portions being integral with one of said rod engaging portions distal from said central portion; and rod engaging means for variably engaging said plate to each of the pair of rods at a plurality of locations along a corresponding one of said rod engaging portions between said central portion and said fixation element engagement portion, said rod engaging means including clamping means extending through said slot for clamping one of the rods against a surface of said body portion;

wherein said central portion of said plate has a length sufficient to span across the spinous process when said plate is engaged to the pair of rods.

37. A system including a plurality of vertebral fixation elements for attachment to a spine to correct and support the spine in treatment of spinal abnormalities, said system comprising:

a pair of spinal rods;

an elongated plate having a longitudinal length sufficient to span the spinous processes of a patient, and including;

an elongated central portion having opposite ends;

a pair of rod engaging portions, one each integrally disposed at each of said opposite ends of said central portion, each of said rod engaging portions having a longitudinal axis and a plurality of locations adapted to receive a spinal rod, said locations spaced along the longitudinal axis of each of said rod engaging portions; and a fixation element engagement portion for engaging one of the plurality of vertebral fixation elements, having a portion connected with one of said rod engaging portions distal from said central portion, said fixation element engagement portion including means for varying an orientation of the one vertebral fixation element relative to said plate in one linear degree of freedom and two mutually perpendicular rotational degrees of freedom; and means for variably engaging said plate to each of the pair of rods at said plurality of locations along a corresponding one of said rod engaging portions to support said pair of rods at variable distances from each other on opposite sides of the spinous process of the patient.

* * * * *